United States Patent [19]
Pethybridge

[11] Patent Number: 4,721,102
[45] Date of Patent: Jan. 26, 1988

[54] TRACTION DEVICE

[76] Inventor: Bruce Pethybridge, Church Street, Whorouly, Victoria, Australia, 3735

[21] Appl. No.: 910,092

[22] PCT Filed: Dec. 17, 1985

[86] PCT No.: PCT/AU85/00318
§ 371 Date: Aug. 6, 1986
§ 102(e) Date: Aug. 6, 1986

[87] PCT Pub. No.: WO86/03672
PCT Pub. Date: Jul. 3, 1986

[30] Foreign Application Priority Data

Dec. 18, 1984 [AU] Australia ............... PG8618

[51] Int. Cl.⁴ .............................................. A61F 5/02
[52] U.S. Cl. .................................................. 128/78
[58] Field of Search ............................ 128/78, 87 B

[56] References Cited

U.S. PATENT DOCUMENTS

| | | | |
|---|---|---|---|
| 1,722,205 | 7/1929 | Freund | 128/78 |
| 2,820,455 | 1/1958 | Hall | 128/87 B |
| 2,886,031 | 5/1959 | Robbins | 128/78 |
| 3,548,817 | 12/1970 | Mittasch | 128/78 X |
| 3,799,156 | 3/1974 | Gurkin | 128/78 X |
| 3,889,664 | 6/1975 | Heuser et al. | 128/78 R |

FOREIGN PATENT DOCUMENTS 155873 3/1954 Australia .
213056 1/1956 Australia .

Primary Examiner—Charles A. Pearson
Assistant Examiner—Moshe I. Cohen
Attorney, Agent, or Firm—Townsend and Townsend

[57] ABSTRACT

A portable device for placing a part of the body in traction comprises a pair of flexible bands (10, 11) having anchoring means (12, 14) at opposed ends to tightly secure the flexible bands (10, 11) around the body. The device also comprises a number of biasing means (18, 19, 21, 22) received in aligned pockets (16, 17) in the flexible bands (10, 11). Each biasing means comprises a slide housing (18), a slide member (22) and a spring (21) which biases the slide member (22) from the slide housing (18). In use, when the flexible bands (10, 11) are tightly secured around the torso at spaced apart locations the biasing force of the biasing means (18, 19, 21, 22) is distributed around the torso at the spaced locations to place the section of the body between the flexible bands (10, 11) in traction.

4 Claims, 4 Drawing Figures

TRACTION DEVICE

The present invention relates to a traction device and is particularly concerned with a portable device for putting part of the body into traction.

The pain and loss of work days associated with back complaints such as slipped discs is well documented and there have been various proposals for giving temporary relief, including elasticated belts and essentially rigid belts. While these devices may give some support to the back, neither is renowned for its success in easing the pain. Furthermore the essentially rigid belts prevent movement of the back and effectively incapacitate the wearer.

It is an object of the present invention to provide an improved device for easing back and some other body ailments.

According to the present invention there is provided a traction device comprising an upper flexible band, and a lower flexible band means for securing the bands tightly around part of a body, and means extending between the two bands adapted to bias the two bands relatively away from each other.

By the present invention, the upper and lower bands may be worn tightly around the lower chest and waist respectively and be urged apart by the biasing means to provide support for the lower back region. The device may help to slightly separate the vertebrae and thereby relieve pain caused by a slipped disc and at the same time allow the lower back to flex as desired. The device may be suitably adapted for use on the upper back, the neck, or on other parts of the body which require traction. Thus, if the device were used on the neck, the upper and lower flexible bands should be shaped to be received around the chin and back of the head and on the shoulders respectively and have sufficient rigidity to maintain the support so that the biasing means applies traction to the neck. The flexibility would be required in the bands to permit them to be applied on the wearer.

One or both of the bands may be endless and be formed of elastic material or have other fastening means whereby the bands can be fitted onto the wearer and tightened, but preferably each band has opposed end portions and means for fastening the opposed end portions of each band together. The fastening means of each band is preferably separate.

Advantageously the two bands extend generally parallel to each other, and they may be prevented from exceeding a predetermined spacing by one or more lengths of flexible material extending between the upper and lower bands. Conveniently the or each length of flexible material underlies a respective biasing means, that is lies between the biasing means and the skin in use, so that some protection is afforded the wearer. In use of a device in accordance with the invention with such lengths of flexible material extending between the bands, the bands would be fitted to the wearer with the lengths of flexible material slack whereby the aforementioned traction may be applied by the bands. Alternatively the length or lengths of flexible material may be elastic.

Preferably the traction device includes a plurality of biasing means spaced along the bands and advantageously the spacing of the biasing means on opposite sides of an imaginary centerline through each band transverse to the length thereof is equal so that the plural biasing means may be symmetrically disposed about the body. The spacing between the plural biasing means may be adjustable to ensure, for example, that the biasing means do not sit uncomfortably, and this may be performed by adjustment of the biasing means relative to the bands or by taking in and letting out respective portions of the bands.

The biasing means may take any suitable form but in a preferred embodiment may comprise a slide housing supported in one of the flexible bands, a slide member slidably supported by the housing to move towards and away from said one flexible band and engaged with the other of the flexible bands, and spring means in the housing urging the slide member towards said other flexible band. The or each biasing means advantageously has as flat a cross-section as possible so that it does not stand out from the wearer and is preferably flexible or partly flexible to facilitate twisting of the body between the bands.

The traction device of the present invention will now be described by way of example only with reference to the accompanying drawings in which.

Figure 1:
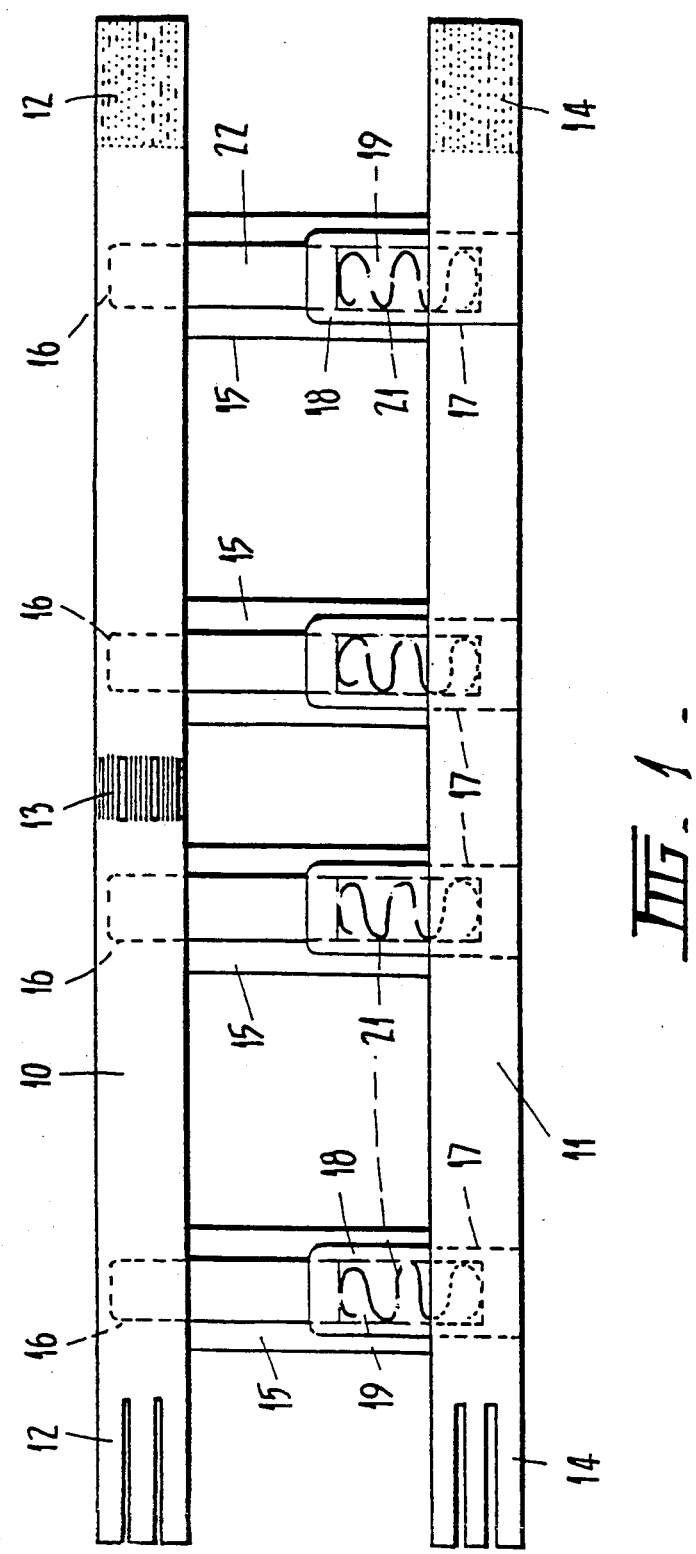
FIG. 1 shows one embodiment of the traction device prepared for use.
Figure 2:
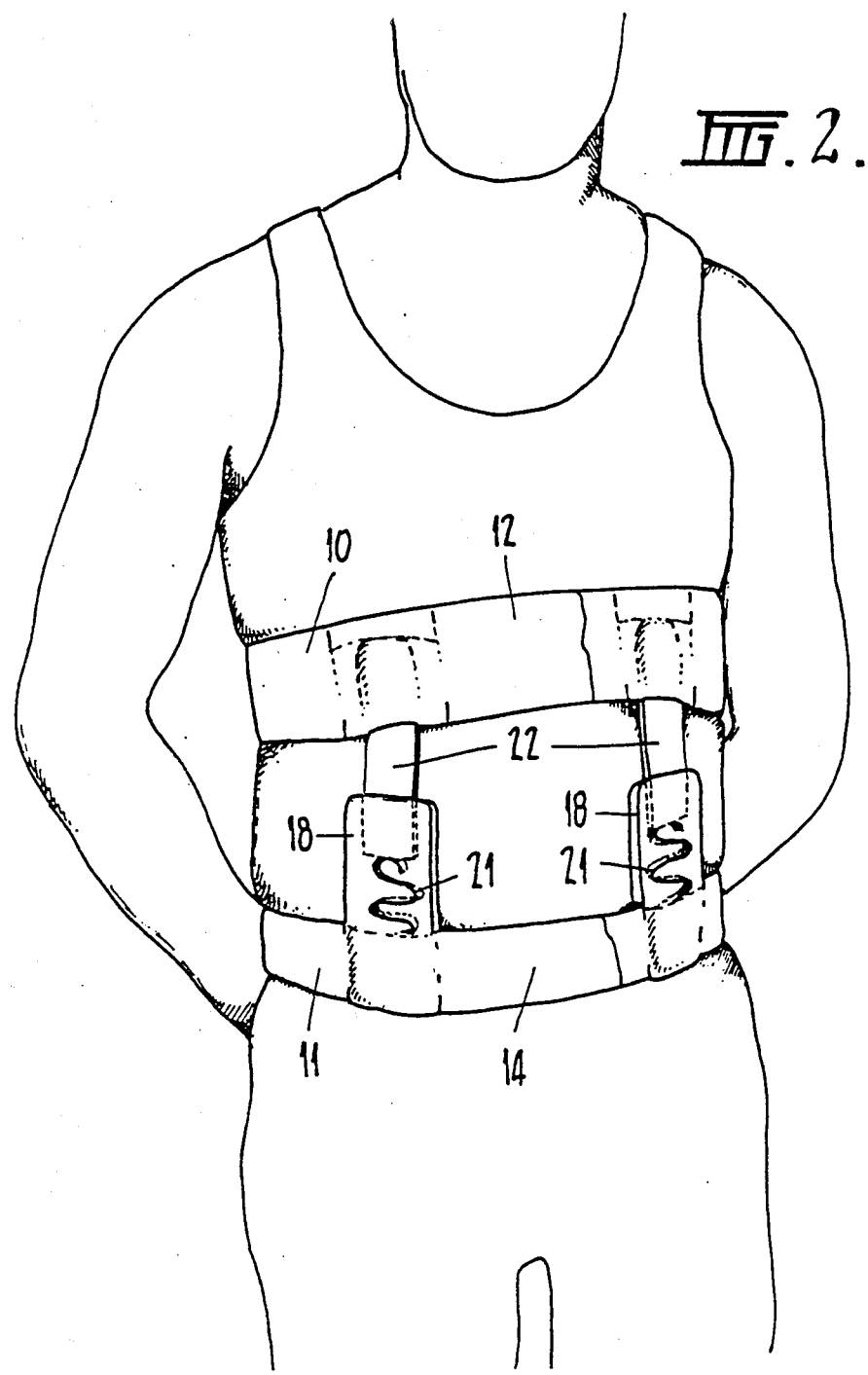
FIG. 2 shows the device shown in FIG. 1 in use.
Figure 3:
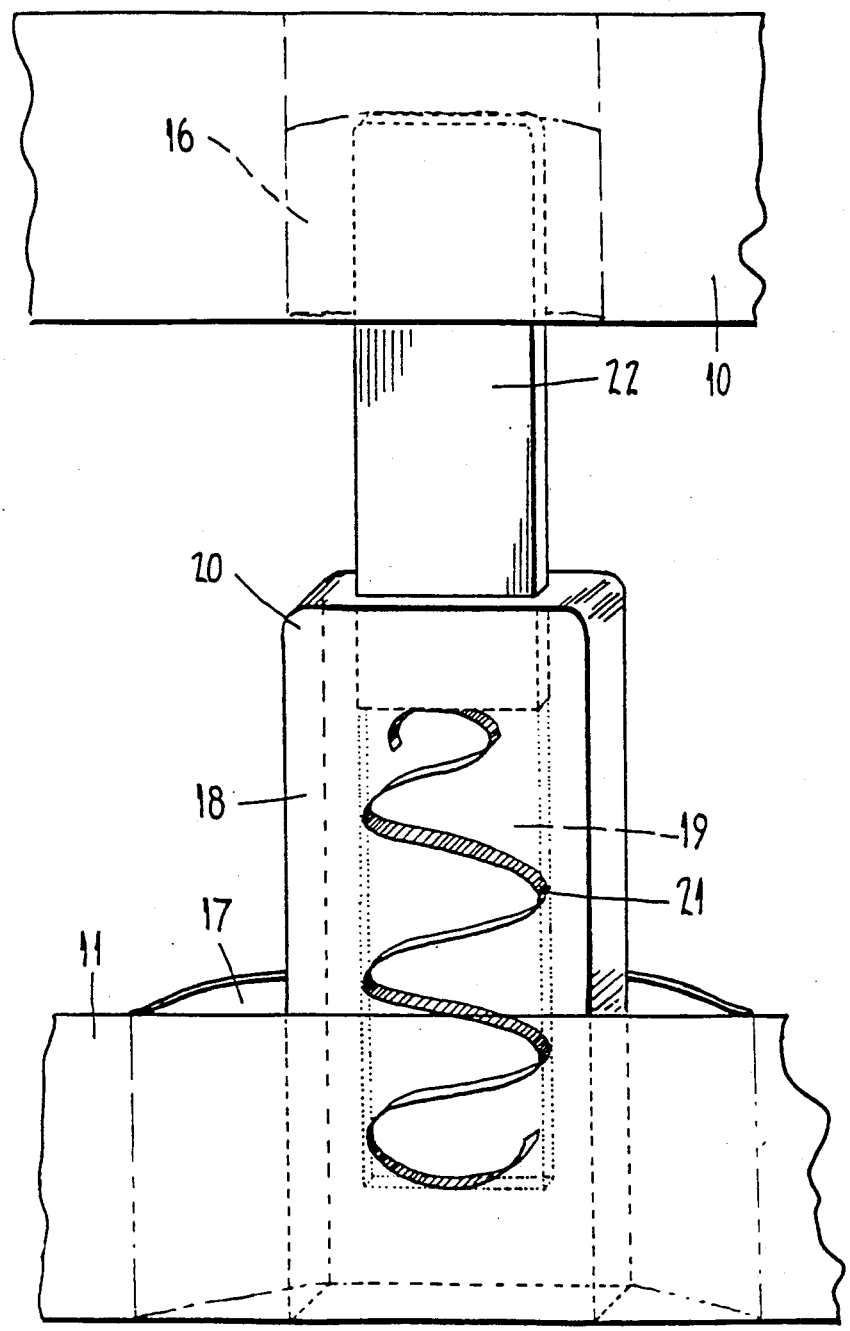
FIG. 3 shows in enlarged manner one of the biasing means in the device shown in FIGS. 1 and 2.

The traction device illustrated in FIGS. 1 to 3 comprises upper and lower bands 10 and 11 respectively. The bands are preferably formed of flexible textile material, and are of elongate nature with sufficient width to be comfortable when worn. In the embodiment illustrated, the upper band 10 is intended to be worn about the lower chest as shown in FIG. 2 and includes fastening means 12 at the opposed ends to enable the band to be secured tightly around the chest and, at its centre, an elastic portion 13 to absorb expansion and contraction of the chest when the band is fitted. The lower band 11 is intended to extend around the waist as shown in FIG. 2 and includes fastening means 14 which enable the lower band to be secured tightly. The fastening means 12 and 14 may include, for example, a buckle arrangement but preferably each comprises a multiple hook and eye assembly such as that marketed under the trademark VELCRO.

The upper and lower bands 10 and 11 extend in generally parallel manner and are restrained from exceeding a maximum spacing by a plurality of straps 15 (shown in FIG. 1 but, for convenience only, not in FIGS. 2 and 3) which extend transversely between the bands. The straps 15 are preferably formed of flexible textile material which permit the bands to be moved towards each other and which are sewn into the bands at respective ends. The straps 15 may include elastic material.

Pockets 16 and 17 (shown most clearly in FIG. 3) are formed in the upper and lower bands 10 and 11 respectively immediately adjacent the position at which the straps 15 are attached to the bands.

Each pocket 17 receives the bottom end of a housing 18 of a biasing means having a slide passage 19 therein which opens at the upper end 20 of the housing. The housing may be moulded in suitable material or may be formed in any other suitable manner. As shown in the drawings the housing may be formed of a transparent material such as perspex. The slide passage 19 has a flat cross-section and has a flat compression spring 21 received in it. The compression spring 21 biases a slide member 22 slidably received in the upper end of the slide passage and projecting from the upper end of the housing into the opposed pocket 16. The slide member 22 is preferably formed from stainless steel, although a strong plastics material could be used. Furthermore, it is preferred that the slide member 22 be flexible or partly flexible to facilitate twisting by the wearer.

The housing 18 and slide member 22 are restrained against movement in the respective pockets 17 and 16 so that any movement by the wearer which causes the portion of the bands 10 and 11 adjacent the particular biasing means to move towards each other acts to displace the slide member 22 into the housing and thereby compress the spring 21.

As shown, four such biasing means are provided, symmetrically spaced about the transverse centrelines of the belts. Accordingly, assuming the compression springs 21 all apply the same force, the biasing means apply an equal traction force around the body when the body is straight. It has been found that such traction force relieves pain caused by a slipped disc in the lower lumbar region, but resting the front pair of housings 18 on the hips is to be avoided since this may abrade and cause soreness. Accordingly, it is preferred that the bands include some means for adjusting the positions of at least the front two biasing means and this may include a buckle arrangement (not shown) on each band to take up slack. Alternatively the respective biasing means may be moved into an another pair of pockets (not shown). Abrasion of the skin caused by relative movement between the housings 18 and slide members 22 is reduced by the flexible straps 15 which underlie the biasing means.

In use, the lower band 11 is fitted first by making any available and necessary adjustment to ensure the front biasing means do not sit on the hips and is then secured tightly around the waist by engaging the fastening means 14. Similar adjustment is then made to the upper band 10 which is then wrapped around the chest with the compression springs 21 under equal compression and the straps 15 slack. The band 10 is then secured tightly around the lower chest by way of the fastening means 12.

Figure 4:
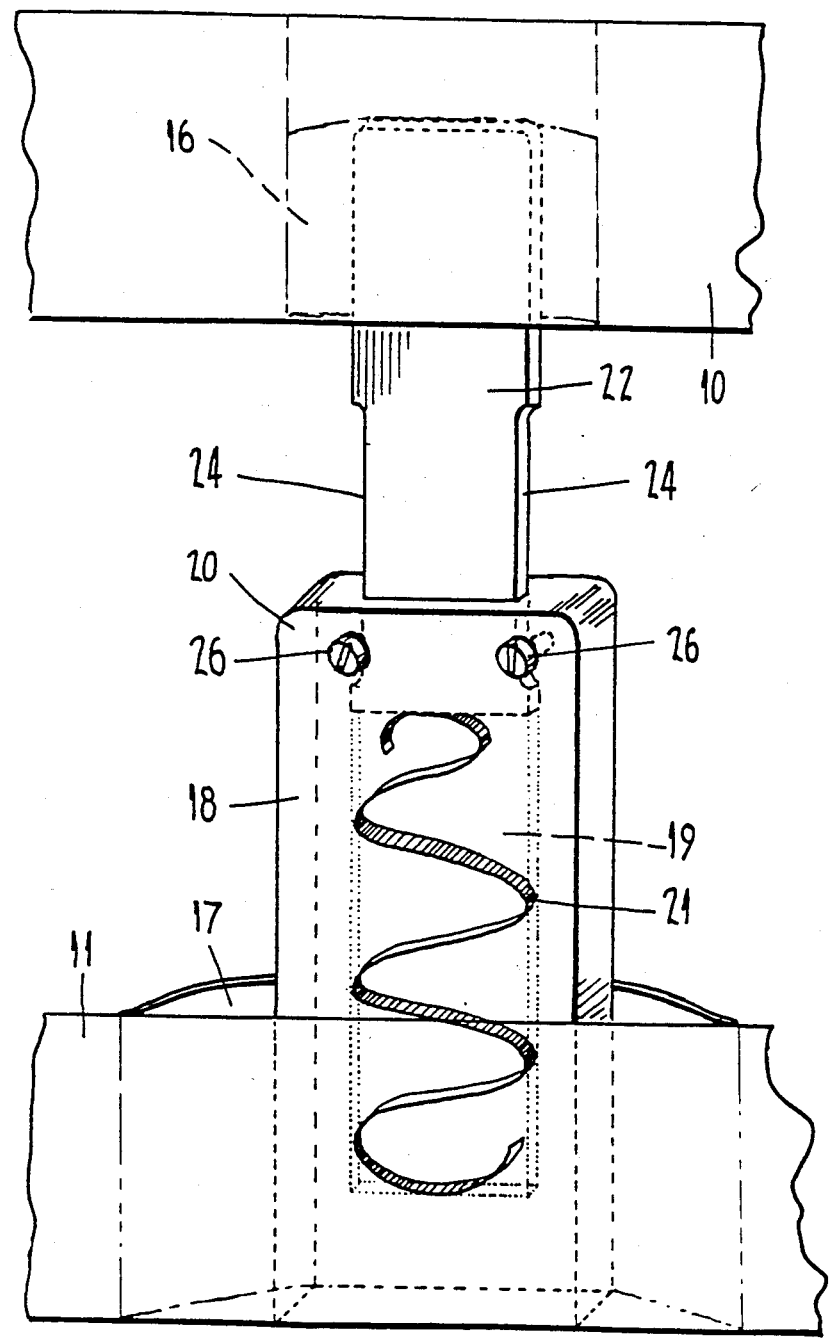
FIG. 4 shows in an enlarged manner a section of another embodiment of the traction device.

In the embodiment shown in FIG. 4, the straps 15 shown in the embodiment described in relation to FIGS. 1 to 3 are replaced by modifying the biasing means. In this regard, the slide member 22 is formed with recesses 24 in each side so that when the slide member 22 initially is positioned to extend into the slide passage 19 two pins 26 are then inserted through openings (not shown) in the housing 18 to reduce the width of the slide passage 19, thereby to prevent withdrawal of the slide member 22 from the housing 18 and to prevent over compression of the spring 21. It can readily be appreciated that such an arrangement restrains the upper and lower bands 10 and 11 from exceeding maximum spacing.

It will be appreciated that many modifications and variations which form part of this invention may be made to the embodiment disclosed above, particularly to adapt the traction device for use on other parts of the body, including limbs and the neck. Such modifications and variations will be apparent to those skilled in the art following a perusal of this specification.

I claim:

1. A traction device comprising:
   an upper flexible band and a lower flexible band extending generally parallel to one another;
   means for securing said bands tightly around the perimeter of the torso of a person to define respective continuous anchoring means for the device at spaced apart locations on the torso;
   straps, connected to the upper and lower bands, for preventing the bands from exceeding a predetermined spacing; and
   a plurality of biasing means coupled to the bands so that the biasing force of the biasing means is distributed around the torso at the spaced apart locations through said tightly secured bands to place the area of the torso between the spaced apart locations in traction, the biasing means being coupled to the bands so that at least two of the biasing means are located at each of the front and back regions of the torso to increasingly support the torso as the person progressively leans forward and backward, the biasing means being formed from material having a generally rectangular cross-section and having a generally flat overall cross-section so as not to stand out from the wearer.

2. The traction device as claimed in claim 1, wherein the biasing means is flexible or partly flexible to facilitate twisting of the body between the bands.

3. The traction device as claimed in claim 1, wherein said biasing means are disposed symmetrically about the body.

4. The traction device as claimed in claim 1, wherein the spacing between the biasing means is adjustable to ensure that the biasing means does not sit uncomfortably.

* * * * *